United States Patent [19]
Martins et al.

[11] Patent Number: 5,306,290
[45] Date of Patent: Apr. 26, 1994

[54] SUTURE BUTTON

[75] Inventors: Harold M. Martins, Newton, Mass.; Stephen J. Snyder, Encino, Calif.

[73] Assignee: Mitek Surgical Products, Inc., Norwood, Mass.

[21] Appl. No.: 17,145

[22] Filed: Feb. 12, 1993

[51] Int. Cl.$^5$ .............................................. A61B 17/00
[52] U.S. Cl. .................................. 606/232; 215/355; 215/309
[58] Field of Search ............... 606/232; 215/307, 309, 215/355

[56] References Cited

U.S. PATENT DOCUMENTS

| 729,835 | 6/1903 | Ruffin et al. | 215/355 |
| 1,577,539 | 3/1926 | Polk | 215/309 |
| 2,148,196 | 2/1939 | Falk | 215/309 |
| 2,537,232 | 1/1951 | Nottingham | 215/355 |
| 4,715,359 | 12/1987 | Ryo | 215/309 |
| 5,156,616 | 10/1992 | Meadows et al. | 606/232 |
| 5,217,486 | 6/1993 | Rice et al. | 606/232 |

Primary Examiner—Stephen C. Pellegrino
Assistant Examiner—Gary Jackson
Attorney, Agent, or Firm—Pandiscio & Pandiscio

[57] ABSTRACT

A suture retaining device in the form of a frusto-conical button having parallel upper and lower planar surfaces which are connected together by a conical surface. The button is provided with a recessed chamber for substantially completely accommodating one or more suture knots. At least one hole is formed in the button leading from the recessed chamber to the lower planar surface, and at least one hole is formed in said button leading from the recessed chamber to the conical surface.

26 Claims, 4 Drawing Sheets

SUTURE BUTTON

FIELD OF THE INVENTION

This invention relates to surgical devices in general, and more particularly to surgical washers or buttons to be employed in connection with sutures and suture-like elements.

BACKGROUND OF THE INVENTION

Many devices are currently available for use in effecting surgical attachments, particularly in attaching objects to bone.

In some procedures, for example, a hole is first drilled in a bone, and then a suture anchor is deployed in the hole, with a suture element trailing from the suture anchor and extending out of the bone. Tissue or other objects may then be secured to the bone using the suture. In some cases the suture may extend completely around the tissue or other object which is being attached to the bone; in other cases the suture may be passed through the tissue or other object and then tied off on the far side of the tissue or object so as to effect attachment. In the case where the suture extends through the tissue or other object and is tied off on the far side thereof, various types of washers or buttons have been proposed to facilitate attachment. These washers or buttons rest against the outer surface of the tissue or other object, and improve the connection between the suture and the tissue or object.

The need for such secure attachment is particularly critical in connection with reapproximating bone of any type to another bone. This type of procedure is exemplified in applications such as joining the fibula to the tibia bone in ankle surgery, or as applied to a shoulder operation. In the case of acromioclavicular and coracoclavicular suture fixations, for example, several holes are drilled in the clavicle above the coracoid. A suture is passed beneath the base of the coracoid and superiorly through the two holes in the clavicle. Another suture is attached to the acromioclavicular ligament and then attached to the clavicle. The joint is then reduced and the sutures are tied off. Sutures such as mattress sutures may be placed in any ruptured coracoclavicular ligaments and also tied off. In addition, the ligaments may be joined to the bone by the same technique.

This procedure is significantly improved by the use of suture anchors, which can be recessed into the coracoid and the suture extended superiorly through only a single hole in the clavicle. This eliminates the need to place a suture exteriorly of the coracoid and thereby removes the possibility of the suture subsequently eroding because of motion in the shoulder.

Even with this improved procedure, however, there still remains the necessity of tying off the suture. As indicated above, conventional surgical buttons, washers or other suture retaining devices may be used, where the suture is pulled through the retaining device and tension then applied to the tissue before the suture is tied off.

One such type of suture retaining device is shown in U.S. Pat. No. 4,741,330 issued May 3, 1988 to Hayhurst. As taught in this patent, the suture retaining device is a button of resilient material having slits formed therein which cross at the center of the button, in order to create pointed bendable flaps. The suture is inserted through the center of the button and the flaps are resiliently deformed away from the plane of the button, toward the direction of movement of the suture. Thereafter, the button is urged toward the surface of the tissue which is to be joined to a bone and, after tension is applied to the suture while pushing against the button, the suture is tied off so as to hold the tissue securely against the bone.

In another type of retaining device, as exemplified by U.S. Pat. No. 4,669,473 issued Jun. 2, 1987 to Richards et al., the suture (or filament) is provided with a plurality of conically shaped ribs along its length. The ribs are formed so that the larger end of each rib faces toward the tissue or bone. Such ribs allow an associated flexible washer to be slid over the suture (or filament) and over the ribs in the direction of the tissue or bone, yet prevent the washer from slipping backward over a conically shaped rib once it has passed that rib. In this manner the washer can be brought to bear against the tissue and held there by the nearest conical rib.

In all of the known prior art suture retaining devices, there remains the drawback that the buttons or washers, as well as the suture knots, are left protruding above the superior tissue or bone surface at the conclusion of the procedure. As a result, the buttons and/or knots may cause trauma to a patient when the joint or body part is thereafter subjected to movement.

It is, therefore, one object of the present invention to provide a suture retaining device which permits the suture knot to be recessed below the top surface of the tissue or bone element which is being approximated to another bone using suture.

Another object of the present invention is to provide a suture retaining device which is itself capable of being disposed below the superior surface of the tissue or bone element which is being approximated to another bone using suture.

Still another object of the present invention is to provide a suture retaining device for use with a suture anchor, wherein both the suture knot customarily employed in tying off the suture, as well as the retaining device itself, are both embedded below the tissue or bone surface.

A further object of the present invention is to provide a suture retaining device which permits ligaments to be transversely attached to a bone by means of a side hole or holes formed in the suture retaining device.

A still further object of the present invention is to provide a suture retaining device for use in fixedly holding ligament graft material within a bone tunnel.

And another object of the present invention is to provide a suture retaining device which may be used with at least one length of suture to approximate an object to an anatomical structure.

SUMMARY OF THE INVENTION

These and other objects of the present invention are achieved by providing a novel suture retaining device which is in the form of a conical washer or button element. The button element has a recessed area for accommodating one or more suture knots within the interior of the element. In addition, the conical button may be embedded in a pre-drilled and counterbored (or countersunk) hole in the bone or other object which is being attached, so that the conical button, as well as the one or more suture knots contained therein, is disposed below the bone's (or object's) top surface.

BRIEF DESCRIPTION OF THE DRAWINGS

These and other objects and features of the present invention are more fully disclosed or rendered obvious by the following detailed description of a preferred embodiment of the invention, which is to be considered together with the accompanying drawings wherein like numbers refer to like parts, and further wherein.

DETAILED DESCRIPTION OF THE INVENTION

Figure 1:
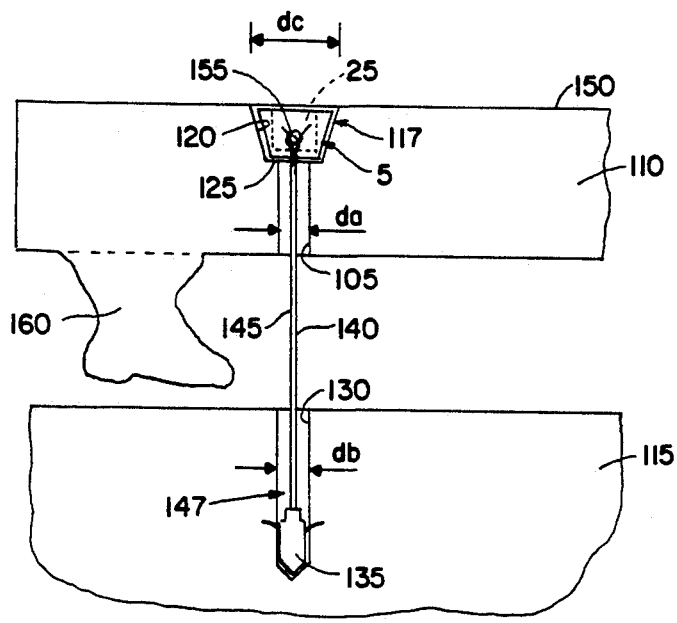
FIG. 1 is a cross-sectional view illustrating the attachment of one bone to another bone using the suture retaining device of the present invention.
Figure 2:
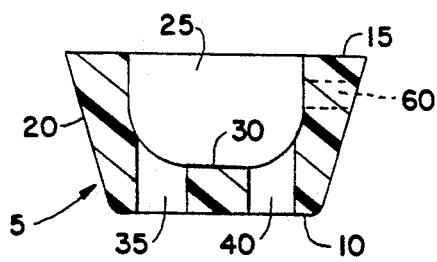
FIG. 2 is a cross-sectional view of a preferred embodiment of the suture retaining device of the present invention.
Figure 3:
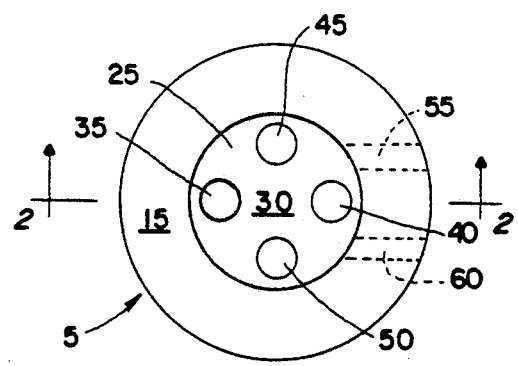
FIG. 3 is a top view of the same suture retaining device.
Figure 4:
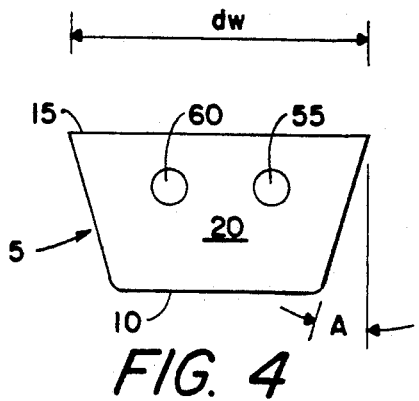
FIG. 4 is a side view of the same suture retaining device.

Looking first at FIGS. 1, 2, 3 and 4, there is shown a frusto-conical button or washer 5 which constitutes a preferred embodiment of the present invention. Button 5 comprises lower and upper parallel planar surfaces 10 and 15, respectively, which are joined by a conical outer surface 20. The slope of outer surface 20 may vary depending on the particular application involved. In general, the slope of outer surface 20 is chosen so as to provide the smallest possible outside diameter for upper planar surface 15 (i.e., the dimension "dw" in FIG. 4), while still providing surface 20 with a slope sufficient to permit it to act as an effective bearing surface to transfer load to the recipient bone. By way of example but not limitation, it has been found that satisfactory buttons have been formed where the slope of surface 20 relative to the vertical (i.e., the angle "A" in FIG. 4) is as small as 15° or as large as 45°.

Button 5 is preferably made of a biocompatible plastic material such as polysulfone, acetyl polymers, polyamides or any one of the many other well known biocompatible plastic materials. Alternatively, button 5 could also be formed out of a biocompatible metal, a biocompatible ceramic or a biocompatible absorbable material, all of which materials are well known in the art.

Button 5 is formed with an internal chamber 25 which extends downward from top planar surface 15 toward, but which does not meet, lower planar surface 10. Internal chamber 25 terminates in a floor 30. Chamber 25 is sized so that it can accommodate one or more suture knots within the body of button 5, as seen, for example, in FIG. 1 and as will hereinafter be described and illustrated in further detail.

In order to provide access for a suture to the internal chamber 25, at least one and preferably at least a pair of bottom holes 35 and 40 (see FIGS. 2 and 3) are provided. These holes extend from bottom surface 30 of chamber 25 through planar bottom surface 10, so as to permit the interior of chamber 25 to communicate with the region below bottom surface 10. The ability of the suture button to accommodate additional sutures may be achieved by providing the additional holes 45 and 50 (see FIG. 3) through floor 30 and bottom surface 10.

Additional suture attachments may also be accomplished by providing the side holes 55 and 60 (see FIGS. 2-4) in conical surface 20 of button 5, as will hereinafter be described in further detail.

The device of the present invention can be used to approximate a variety of objects to various anatomical structures. The device is especially useful in reapproximating bone of any type to bone, such as in the shoulder or ankle. It could also be used to secure ligament graft material in a bone tunnel.

One manner of employing the suture retaining device of the present invention can be conveniently illustrated with reference to U.S. patent application Ser. No. 07/902,513, filed Jun. 22, 1992 by Lehmann K. Li, and assigned to the assignee of this patent application. As taught in U.S. patent application Ser. No. 07/902,513, a suture anchor can be deployed into a bone so that two free ends of suture extend outside the bone and can be used to attach various objects to the bone. For example, the two free ends of suture might be used to attach another bone to the bone which has received the suture anchor. Such an arrangement is illustrated in FIG. 1; FIG. 1 also shows how the suture receiving button 5 may be advantageously employed in such a situation.

More particularly, and with reference now to FIG. 1, a hole 105 is first drilled completely through a bone 110 which is to be reapproximated to another bone 115. The upper end of hole 105 is then counterbored at 117 so as to provide a sloped side wall surface 120 terminating in an annular end surface 125. Annular end surface 125 extends between sloped side wall surface 120 and hole 105. Counterbore 117 is formed so that the bone's sloped side wall surface 120 is disposed at substantially the same angle as the button's outer surface 20, and so that the hole's outermost diameter (i.e., the dimension "dc" in FIG. 1) is larger than the button's maximum diameter (i.e., the dimension "dw" in FIG. 4). In this way button 5 can be completely received in counterbore 117 and make a flush fit with the walls of the counterbore, as will hereinafter be described in further detail. Finally, a hole 130 is drilled into bone 115. Hole 130 is drilled so that its diameter is less than the diameter of hole 105 (i.e., so that the dimension "db" in FIG. 1 is less than the dimension "da" in FIG. 1). Thus, it will be seen that, in terms of relative dimensions, "dc">"dw">"da">"db".

A barbed suture anchor 135 may then be deployed in hole 130 in the manner taught in the aforementioned U.S. patent application Ser. No. 07/902,513, whose disclosure is hereby incorporated herein by reference. By forming the hole 105 in bone 110 large enough relative to hole 130 in bone 115, suture anchor 135 can pass easily through hole 105 while still lodging itself in the desired manner in hole 130 in bone 115. The free ends 140 and 145 of the suture 147 which is attached to the suture anchor 135 will then extend outwardly from bone 115 and through hole 105 in bone 110, so that they sit above the superior surface 150 of bone 110.

The free ends 140 and 145 of suture 147 are then threaded through the button's bottom holes 35 and 40, respectively. Then button 5 is slid down the suture strands until the button is seated in counterbore 117 so that the button's bottom surface 10 comes to rest on annular surface 125. As this occurs, the button's sloped outer surface 20 will make a flush engagement with the counterbore's sloped side wall surface 120, whereby load may be efficiently transferred from button 5 to bone 110 when tension is placed on suture 147. At the same time, it will also be appreciated that when the button's bottom surface 10 is in engagement with the bone's annular surface 125, the button's upper planar surface 15 will lie below the top surface 150 of bone 110.

At this point bone 110 is adjusted into its desired position relative to bone 115, if it is not already in this position. Then the free ends 140 and 145 of suture 147 are drawn taught and tied off into a knot 155, with the knot 155 resting against the button's floor 30 and being accommodated completely within the button's internal chamber 25. In this way suture 147 will maintain bone 110 in the desired position relative bone 115, with ligament 160 of bone 110 lying adjacent to bone 115 for subsequent healing. As this occurs, button surfaces 10 and 20 will efficiently distribute the load of the taught suture 147 onto bone surfaces 125 and 120, respectively. At the same time, both the top surface 15 of button 5, as well as the knot 155, will be positioned below top surface 150 of bone 110.

Figure 5:
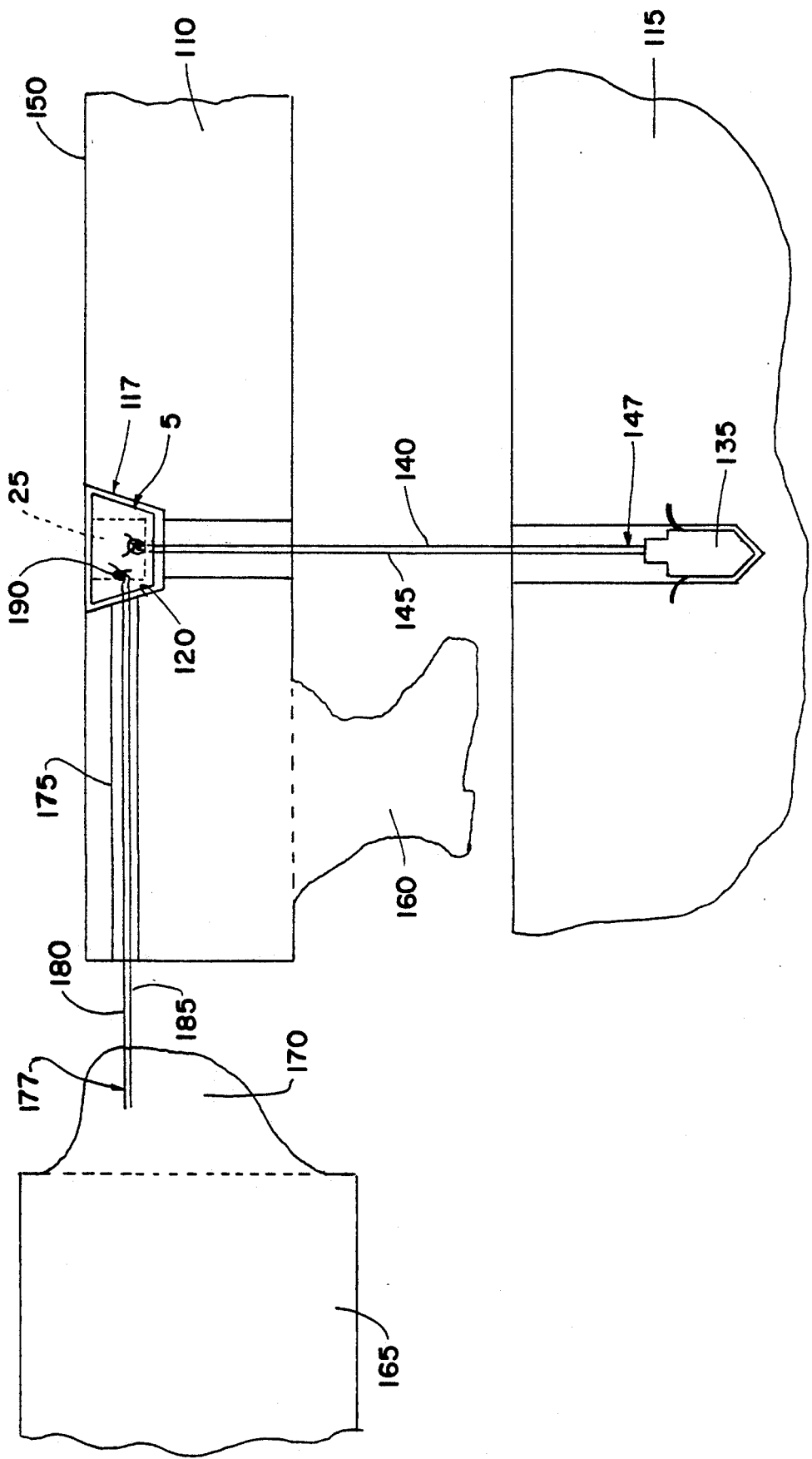
FIG. 5 is a cross-sectional view similar to that of FIG. 1 but showing the transverse attachment of an additional bone by using an additional suture with the same suture retaining device.

As shown in FIG. 5, an additional bone 165 carrying a ligament portion 170 may also be approximated to bone 110 using button 5. More particularly, a hole 175 is drilled laterally through bone 110 so that it intersects the counterbore's sloped side wall surface 120 adjacent to the location where the button's side holes 55 and 60 will lie when button 5 is disposed in counterbore 117. Then a suture 177 can be attached to ligament 170, and the free ends 180 and 185 of that suture drawn through hole 175, and then through the button's side holes 55 and 60. This is typically done before button 5 is disposed in counterbore 117. Thereafter, when button 25 is seated in the bone's counterbore 117, suture 177 can be appropriately tensioned and the ends of that suture tied off into a knot 190 so as to keep bone 165 laterally approximated to bone 110. It will be appreciated that knot 190 will also lie within the button's internal recess 25, so that it is recessed below the top surface 150 of bone 110.

Figure 6:
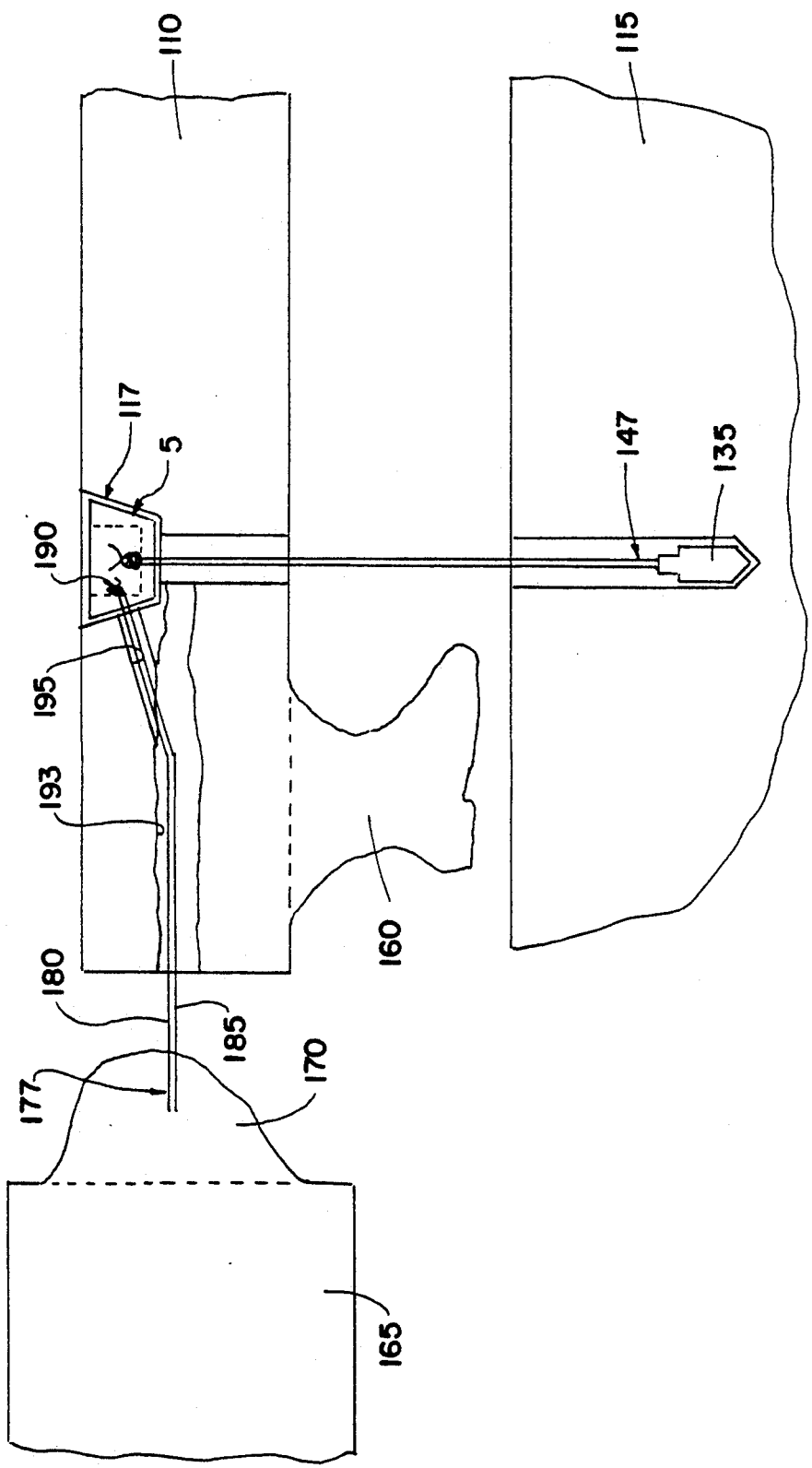
FIG. 6 is a cross-sectional view similar to that of FIG. 5 but showing the use of the intramedullary canal when effecting the transverse attachment of that additional bone.

Looking next at FIG. 6, the intramedullary canal 193 in bone 110 may be employed if it is desired to avoid drilling the lateral hole 175 (see FIG. 5) in bone 110. Where this is done, a smaller angled access hole 195 is drilled from the counterbore's sidewall surface 120 to the canal 193. Access hole 195 is drilled so that it intersects sidewall surface 120 adjacent to where the button's side holes 55 and 60 will lie when button 5 is installed in counterbore 117. In use, a suture 177 is affixed to ligament 170, the suture strands 180 and 185 are drawn through intramedullary canal 193, through access hole 195, and then through holes 55 and 60 in button 5. Again, this is typically done before button 5 is disposed in counterbore 117. Thereafter, when button 5 is seated in the bone's counterbore 117 and the suture 177 is appropriately tensioned, the ends of the suture can be tied into the desired knot 190 so as to keep bone 165 transversely approximated to bone 110.

In the foregoing examples of FIGS. 5 and 6, bone 165 is shown connected to bone 110 by attaching suture 177 to ligament 170 and then to button 5. It is to be appreciated, however, that suture 177 need not necessarily be attached to bone 165 in that particular manner. Alternatively, suture 177 could be connected to bone 165 via a bone anchor (not shown) which is deployed into an appropriate hole (not shown) in bone 165, or suture 177 could be connected to bone 165 in any one of the many other ways well known in the art.

Suture retaining button 5 can also be used to hold graft material in a bone tunnel, e.g. during reconstructive surgery.

Figure 7:
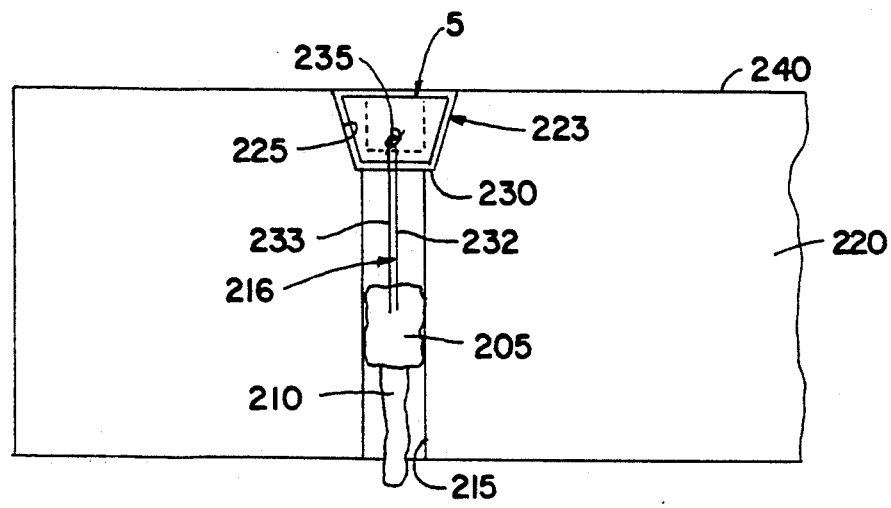
FIG. 7 is a cross-sectional view illustrating the use of a suture retaining device to anchor a bone plug in a bone tunnel.

For example, in FIG. 7, a bone plug 205, having a ligament 210 attached thereto, is shown being held in a bone tunnel 215 by means of button 5 and a suture 216. In such an application, the bone tunnel 215 is first drilled into the recipient bone 220. Tunnel 215 is then counterbored at its top end at 223 so as to create the sloped side wall surface 225 terminating in an annular shoulder 230. Free ends 232 and 233 of suture 216 are connected to the bone plug 205, drawn upward through bone tunnel 215, and then threaded through the button's bottom holes 35 and 40, respectively. Thereafter, button 5 is seated in the bone tunnel's counterbore 223 so that the button's sloped surface 20 seats on the bone's inclined surfaces 225, and so that the button's bottom surface 10 seats on the bone's annular surface 230. The suture 216 is then appropriately tensioned and the suture ends 232 and 233 tied off into a knot 235, so as to hold bone block 205 (and its associated ligament 210) appropriately positioned in bone tunnel 215. Again, it will be appreciated that both button 5 and knot 235 will be positioned below the top surface 240 of bone 220.

Figure 8:
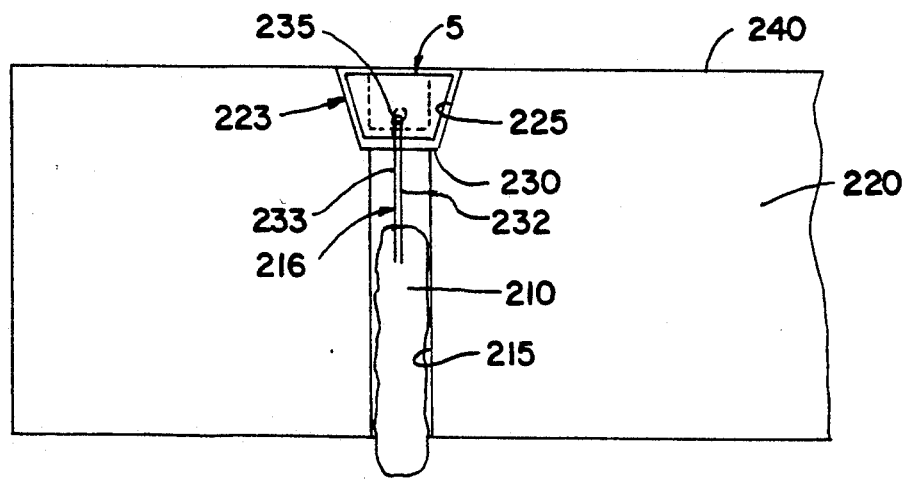
FIG. 8 is a cross-sectional view similar to that of FIG. 7 illustrating the use of a suture retaining device to anchor a piece of soft tissue in a bone tunnel.

FIG. 8 shows an arrangement identical to that of FIG. 7, except that the bone block 205 has been omitted and the suture lengths 232 and 233 are connected directly to the ligament 210.

What has been described above is a preferred embodiment of a novel suture button and a method of its use in a semi-rigid fixation technique. It is to be appreciated, of course, that various changes may be made in the configuration of this button, the materials it is made of and the manner in which it is used, all without departing from the spirit and scope of the present invention.

Thus, for example, while in the example of FIGS. 1 and 5-8, the button 5 is shown deployed into a bone, it is to be appreciated that button 5 could be deployed into a piece of soft tissue, e.g. a ligament. In this case the seat for button 5 might be formed naturally as the resilient tissue simply gives way to the button as the button is forced into the tissue or, if the tissue lacks the necessary resiliency for this, the seat for button 5 might be formed by cutting away the tissue as necessary. Alternatively, button 5 could be used to attach some other object to an anatomical structure, e.g. button 5 could be used to attach a prosthetic device to an anatomical structure.

Also, while in the foregoing example of FIGS. 1 and 5-8, bones 110 and 220 have been shown and described as being counterbored so as to create a seat for button 5 which has both a sloped side wall and an annular base, it is possible for the seat to be formed as a countersink. In this case the seat would have a sloped side wall for engaging the button's sloped side wall 20, but would it not have an annular surface for engaging the button's bottom surface 10.

These and other changes of their type are all considered to be within the scope of the present invention.

What is claimed is:

1. A suture retention means for use in approximating an object to an anatomical structure by at least one length of suture extending outwardly from said anatomical structure and through said object, said suture retention means comprising:

a substantially frusto-conical body having a longitudinal axis, a top surface, a bottom surface, a side surface and a longitudinally-centered cavity extending into said top surface;

said top and bottom surfaces each (a) being substantially planar, (b) being oriented in spaced, parallel relation to one another, and (c) defining a substantially circular periphery centered about said longitudinal axis, said periphery of said bottom surface being smaller than said periphery of said top surface;

said side surface extending in a substantially frusto-conical monomer between said periphery of said top surface and said periphery of said bottom surface;

said longitudinally-centered cavity including a base surface, a sidewall surface and an open end; and said body further defining at least one opening extending from said bottom surface to said base surface, each said opening being sized so as to allow at least one free end of at least one length of suture to be threaded therethrough from said bottom surface into said longitudinally-centered cavity, and so as to prevent a knot formed by said at least one free end of suture from passing therethrough.

2. The suture retention means of claim 1 wherein said body further defines at least one side opening extending from said side surface to said sidewall surface, each said side opening being sized so as to allow at least one free end of at least one second length of suture to be threaded therethrough from said side surface into said longitudinally-centered cavity, and so as to prevent a knot formed by said free end of said at least one second length of suture from passing therethrough.

3. The suture retention means of claim 1 wherein said longitudinally-centered cavity is sized so as to substantially completely contain said knot formed by said at least one free end of said at least one length of suture when said knot abuts said base surface adjacent the opening through which its associated at least one length of suture extends.

4. The suture retention means of claim 2 wherein said longitudinally-centered cavity is sized so as to substantially completely contain said knots formed (a) in said at least one free end of said at least one suture, and (b) in said at least one free end of said at least one second length of suture when said knots abut said base surface and said sidewall surface, respectively, adjacent the openings through which their associated at least one length of suture or at least one second length of suture extend.

5. A suture retention means for use in approximating an object to an anatomical structure by at least one length of suture extending outwardly from said anatomical structure and through said object, said suture retention means comprising:

a substantially frusto-conical body having a longitudinal axis, a top surface, a bottom surface, a side surface and a longitudinally-centered cavity extending into said top surface;

said top and bottom surfaces each (a) being substantially planar, (b) being oriented in spaced, parallel relation to one another, and (c) defining a substantially circular periphery centered about said longitudinal axis, said periphery of said bottom surface being smaller than said periphery of said top surface;

said side surface extending between said periphery of said top surface and said periphery of said bottom surface;

said longitudinally-centered cavity including a base surface, a sidewall surface and an open end; and said body further defining at least one opening extending from said side surface to said sidewall surface, each said opening being sized so as to allow at least one free end of at least one length of suture to be threaded therethrough from said side surface into said longitudinally-centered cavity, and so as to prevent a knot formed by said at least one free end of suture from passing therethrough.

6. The suture retention means of claim 5 wherein said longitudinally-centered cavity is sized so as to substantially completely contain said knot formed by said at least one free end of said at least one length of suture when said knot abuts said sidewall surface adjacent the opening through which its associated at least one length of suture extends.

7. A method for approximating an object to an anatomical structure by at least one length of suture extending outwardly from a surface of said anatomical structure, wherein said object has a first surface and a second surface, said method comprising the steps of:

(a) providing suture retention means comprising:

a substantially frusto-conical body having a longitudinal axis, a top surface, a bottom surface, a side surface and a longitudinally-centered cavity extending into said top surface;

said top and bottom surfaces each (a) being substantially planar, (b) being oriented in spaced, parallel relation to one another, and (c) defining a substantially circular periphery centered about said longitudinal axis, said periphery of said bottom surface being smaller than said periphery of said top surface;

said side surface extending between said periphery of said top surface and said periphery of said bottom surface;

said longitudinally-centered cavity including a base surface, a sidewall surface and an open end; and said body further defining at least one opening extending from said bottom surface to said base surface, each said opening being sized so as to allow at least one free end of at least one length of suture to be threaded therethrough from said bottom surface into said longitudinally-centered cavity, and so as to prevent a knot formed by said at least one free end of suture from passing therethrough;

(b) forming an opening in said object extending from said first surface to said second surface;

(c) countersinking said opening in said object adjacent said first surface so as to form an inclined surface, with the countersunk region being sized so as to substantially completely accommodate said body when said side surface of said body is in engagement with said inclined surface;

(d) locating said object and said anatomical structure in a predetermined position relative to one another, and passing said at least one free end of said at least one length of suture through at least a portion of said opening in said object so as to extend outwardly from said countersunk region;

(e) locating said body in said countersunk region of said opening, with said at least one free end of said at least one length of suture extending through said at least one opening in said body, and tensioning said at least one length of suture; and (f) forming a knot in said at least one free end of said at least one length of suture such that said at least one length of suture is maintained under tension when said knot abuts the portion of said base of said cavity adjacent the opening with which said at least one free end of said at least one length of suture is associated.

8. The method of claim 7 wherein said body further defines at least one side opening extending from said side surface to said sidewall surface, each said side opening being sized so as to allow at least one free end of at least one second length of suture to be threaded therethrough from said side surface into said cavity, and so as to prevent a knot formed by said free end of said at least one second length of suture from passing therethrough, and said method includes the additional steps of:

(i) forming a second opening in said object extending from a surface thereof to said countersunk region;

(ii) locating a second anatomical structure having at least one free end of at least one second length of suture extending outwardly from a surface thereof in a predetermined position relative to said object such that said at least one free end of said at least one second length of suture extends outwardly from said inclined surface of said countersunk region;

(iii) locating said body in said countersunk region of said opening, with said at least one free end of said at least one second length of suture extending through said at least one side opening in said body, and tensioning said at least one second length of suture; and (iv) forming a knot in said at least one free end of said at least one second length of suture such that said at least one second length of suture is maintained under tension when said knot abuts the portion of said sidewall surface of said cavity adjacent the second opening with which said at least one free end of said at least one second length of suture is associated.

9. The method of claim 8 wherein said object is bone and said second opening in said object comprises the intramedullary canal of said bone.

10. A method for approximating an object to an anatomical structure by at least one length of suture extending outwardly from a surface of said anatomical structure, wherein said object has a first surface and a second surface, said method comprising the steps of:

(a) providing suture retention means comprising:

a substantially frusto-conical body having a longitudinal axis, a top surface, a bottom surface, a side surface and a longitudinally-centered cavity extending into said top surface;

said top and bottom surfaces each (a) being substantially planar, (b) being oriented in spaced, parallel relation to one another, and (c) defining a substantially circular periphery centered about said longitudinal axis, said periphery of said bottom surface being smaller than said periphery of said top surface;

said side surface extending between said periphery of said top surface and said periphery of said bottom surface;

said longitudinally-centered cavity including a base surface, a sidewall surface and an open end; and said body further defining at least one opening extending from said side surface to said sidewall surface, each said opening being sized so as to allow at least one free end of at least one length of suture to be threaded therethrough from said side surface into said longitudinally-centered cavity, and so as to prevent a knot formed by said at least one free end of suture from passing therethrough.

(b) forming an opening in said object extending inwardly from said first surface;

(c) countersinking said opening in said object adjacent said first surface so as to form an inclined surface, with the countersunk region being sized so as to substantially completely accommodate said body when said side surface of said body is in engagement with said inclined surface;

(d) forming a second opening in said object extending from said second surface to said inclined surface of said countersunk region;

(e) locating said object and said anatomical structure in a predetermined position relative to one another, and passing said at least one free end of said at least one length of suture through at least a portion of said second opening in said object so as to extend outwardly from said countersunk region;

(f) locating said body in said countersunk region of said opening, with said at least one free end of said at least one length of suture extending through said at least one opening in said body, and tensioning said at least one length of suture; and (g) forming a knot in said at least one free end of said at least one length of suture such that said at least one length of suture is maintained under tension when said knot abuts the sidewall surface of said longitudinally-centered cavity adjacent the opening with which said at least one free end of said at least one length of suture is associated.

11. The suture retention means of claim 1 wherein said object comprises bone.

12. The suture retention means of claim 1 wherein said object comprises soft tissue.

13. The suture retention means of claim 1 wherein said anatomical structure comprises bone.

14. The suture retention means of claim 1 wherein said anatomical structure comprises soft tissue.

15. The suture retention means of claim 14 wherein said soft tissue comprises a length of ligament material.

16. The suture retention means of claim 15 wherein said length of ligament material extends outwardly from a piece of bone.

17. The suture retention means of claim 16 wherein said anatomical structure further comprises a bone plug attached to one end of said length of ligament material.

18. The suture retention means of claim 1 wherein said object defines a hole extending therethrough, and said anatomical structure has a portion adapted to extend into said hole.

19. The method of claim 7 wherein said object comprises bone.

20. The method of claim 7 wherein said object comprises soft tissue.

21. The method of claim 7 wherein said anatomical structure comprises bone.

22. The method of claim 7 wherein said anatomical structure comprises soft tissue.

23. The method of claim 22 wherein said soft tissue comprises a length of ligament material.

24. The method of claim 23 wherein said length of ligament material extends outwardly from a piece of bone.

25. The method of claim 24 wherein said anatomical structure further comprises a bone plug attached to one end of said length of ligament material.

26. The method of claim 7 wherein said object defines a hole extending therethrough, and said anatomical structure has a portion adapted to extend into said hole.

* * * * *